(12) United States Patent
Martelli et al.

(10) Patent No.: US 8,858,480 B1
(45) Date of Patent: Oct. 14, 2014

(54) ADJUSTABLE, MULTI-AXIS MOTION STABILIZER APPARATUS AND METHOD

(76) Inventors: John D. Martelli, Pensacola, FL (US); Marsha Martelli, Pensacola, FL (US)

( * ) Notice: Subject to any disclaimer, the term of this patent is extended or adjusted under 35 U.S.C. 154(b) by 360 days.

(21) Appl. No.: 13/506,878

(22) Filed: May 22, 2012

(51) Int. Cl.
*A61F 5/00* (2006.01)

(52) U.S. Cl.
USPC ................................. 602/16; 602/20; 602/23

(58) Field of Classification Search
USPC ...................... 602/16, 20–28; 128/882; 5/624
See application file for complete search history.

(56) References Cited

U.S. PATENT DOCUMENTS

| | | | |
|---|---|---|---|
| 621,366 A * | 3/1899 | Olsen | 602/16 |
| 5,086,760 A * | 2/1992 | Neumann et al. | 602/27 |
| 5,542,774 A * | 8/1996 | Hoy | 403/116 |
| 8,105,255 B2 * | 1/2012 | Panzer et al. | 602/16 |
| 2006/0287624 A1 * | 12/2006 | Popp et al. | 602/16 |

* cited by examiner

*Primary Examiner* — Michael A. Brown
(74) *Attorney, Agent, or Firm* — J. Nevin Shaffer, Jr.

(57) ABSTRACT

An adjustable, multi-axis, motion stabilizer apparatus and method includes a first curved cup with a curved radius, the first curved cup with an inside surface and an outside surface. A cup hole extends through the first curved cup. A second curved cup is provided, also with a curved radius. The curved radius of the second curved cup is approximately equal to the curved radius of the first curved cup. The second cup also includes an inside surface and an outside surface where the outside surface of the second curved cup fits with the inside surface of the first curved cup. A cup hole is provided in the second curved cup and a pin, conformed to fit in the cup holes, connects the first curved cup with the second curved cup. Also, a size adjustment device is provided for controlling movement of the pin within the cup holes.

20 Claims, 5 Drawing Sheets

ADJUSTABLE, MULTI-AXIS MOTION STABILIZER APPARATUS AND METHOD

FIELD OF THE INVENTION

This invention relates to an adjustable, multi-axis motion stabilizer apparatus and method. In particular, in accordance with one embodiment, the invention relates to an adjustable, multi-axis, motion stabilizer apparatus including a first curved cup with a curved radius, the first curved cup with an inside surface and an outside surface. A cup hole extends through the first curved cup. A second curved cup is provided, also with a curved radius. The curved radius of the second curved cup is approximately equal to the curved radius of the first curved cup. The second cup also includes an inside surface and an outside surface where the outside surface of the second curved cup fits with the inside surface of the first curved cup. A cup hole is provided in the second curved cup and a pin, conformed to fit in the cup holes, connects the first curved cup with the second curved cup. Also, a size adjustment device is provided for controlling movement of the pin within the cup holes.

BACKGROUND OF THE INVENTION

By way of example only and not by way of limitation, a problem exists with regard to rehabilitation after injury or surgery. When a person suffers a knee injury, again for example only, the accepted practice it to stabilize the joint while it heals. Motion of the joint is often completely prohibited for a period of time. Once motion is permitted, prior art devices limit motion in all directions except one, for example, front to back motion only. The range of this motion, by prior art devices, may be gradually increased but is, again, limited to one axis only. Initially, prior art devices, braces and the like, are well suited to helping a user recover gradually from the injury by permitting limited motion in only one direction. A problem has been identified by the Applicants, however, in that a joint in order to fully recover must be allowed to move in any normal direction.

Thus, there is a need in the art for a device that is capable of progressing in range of motion as healing of the joint progresses while still protecting against re-injury due to over extension during healing or after.

It therefore is an object of this invention to provide an adjustable, multi-axis, motion stabilizer apparatus and method that can fully immobilize an appendage such as an arm, leg, or neck, for example only and not by way of limitation, and that can expand its range of motion gradually as the joint heals and which can be used after recovery to allow a full range of motion within a safe injury free range.

SUMMARY OF THE INVENTION

Accordingly, the adjustable, multi-axis, motion stabilizer apparatus of the present invention, according to one embodiment, includes a first curved cup with a curved radius, the first curved cup with an inside surface and an outside surface. A cup hole extends through the first curved cup. A second curved cup is provided, also with a curved radius. The curved radius of the second curved cup is approximately equal to the curved radius of the first curved cup. The second cup also includes an inside surface and an outside surface where the outside surface of the second curved cup fits with the inside surface of the first curved cup. A cup hole is provided in the second curved cup and a pin, conformed to fit in the cup holes, connects the first curved cup with the second curved cup. Also, a size adjustment device is provided for controlling movement of the pin within the cup holes.

All terms used herein are given their common meaning in light of the description herein and in reference to the Figures as more fully set forth hereafter.

In one aspect of the invention, the first cup hole is larger than the second cup hole and the size adjustment device is a shoulder on the pin where the shoulder approximately equals the size of the first cup hole such that the shoulder limits motion to motion in one axis. That is, the pin connects the first cup and the second cup but the first cup is free to move around the pin and in relation to the second cup in one axis only, back and forth.

In another aspect, the shoulder is smaller than the first cup hole such that motion is permitted in more than one axis. Again, the pin joins the two cups together, but in this aspect the pin is free to "wobble" or move in any axis within the first cup hole thus permitting movement in any axis until the pin abuts the sides of the hole in the first cup and is stopped.

In another aspect of the invention, the first cup hole is replaced by a plug recess in the first cup. A plug with a plug hole is provided and the plug is conformed to fit in the plug recess. In this aspect the size of the plug hole limits motion of the pin to motion in one axis only. In a further aspect, the plug hole is larger and motion of the pin is permitted in more than one axis.

Thus, as just set forth, motion of the two cups relative to each other may be limited in at least these two ways: by adjusting the size of the pin shoulder or by changing the size of a plug hole in a plug in the first cup, all as will be more fully describer hereafter with reference to the figures.

In a further aspect, a first extension is connected with the first cup and a second extension is connected with the second cup. The extensions are provided to allow the co joined cups to be secured next to the place they will be used, such as next to a knee joint, for example only. In one aspect, a first unit is formed from a first cup and a second cup and a second unit is formed from another first cup and another second cup where an extension from the first unit is connected with an extension from the second unit. In a further aspect, the first unit and the second unit are positioned with a user appendage there between.

In one aspect, the curved radius is approximately one-half the diameter of the user appendage as will be described more fully hereafter.

According to another embodiment of the invention an adjustable, multi-axis, motion stabilizer apparatus includes a pair of first curved cups with a curved radius, the first curved cups with an inside surface and an outside surface. A cup hole extends through the first curved cups. A pair of second curved cups with a curved radius are provided where the curved radius of the second curved cups is approximately equal to the curved radius of the first curved cups, the second cups with an inside surface and an outside surface where the outside surface of the second curved cups fits with the inside surface of said first curved cups. A cup hole is provided in the second curved cups. A pin is provided that is conformed to fit with the cup holes and movably connect the first curved cups with the second curved cups. Extensions are connected with the first curved cups and with the second curved cups and a size adjustment device is provided for controlling movement of the pin with the cup holes.

In one aspect of this invention, the first cup hole is larger than the second cup hole and the size adjustment device is a shoulder on the pin where the shoulder approximately equals the size of the first cup hole such that the shoulder limits motion to motion in one axis. In another aspect, the shoulder is smaller than the first cup hole such that motion is permitted in more than one axis. In another aspect, the first cup hole is a plug recess in the first cup and further includes a plug with a plug hole, the plug conformed to fit in the plug recess, and the size of the plug hole limits motion of the pin to motion in one axis. In another aspect, the plug hole is larger and motion of the pin is permitted in more than one axis.

In one aspect, an extension from one pair is connected with an extension from another pair and, in use, the pairs are positioned with a user appendage there between. In a further aspect, the curved radius is approximately one-half the diameter of the user appendage.

According to another embodiment of the invention, an adjustable, multi-axis, motion stabilizer method consists of:

a. providing a first curved cup with a curved radius, the first curved cup with an inside surface and an outside surface; a cup hole through the first curved cup; a second curved cup with a curved radius where the curved radius of the second curved cup is approximately equal to the curved radius of the first curved cup, the second cup with an inside surface and an outside surface where the outside surface of the second curved cup fits with the inside surface of the first curved cup; a cup hole in the second curved cup; a pin conformed to fit with the cup holes and connecting the first curved cup with the second curved cup; and a size adjustment device for controlling movement of the pin within the cup holes;

b. connecting the first cup and the second cup to form a first unit and connecting the first unit with a user appendage.

In another aspect of the method, the first cup hole is larger than the second cup hole and the size adjustment device is a shoulder on the pin where when the shoulder approximately equals the size of the first cup hole such that the shoulder limits motion to motion in one axis and where when the shoulder is less than the size of the first cup hole motion is permitted in more than one axis and further including the step of selecting a pin with a desired shoulder size In another aspect, the first cup hole consists of a plug recess in the first cup and further including a plug with a plug hole, the plug conformed to fit in the plug recess, where the plug hole limits motion of the pin to motion in one axis when the plug hole is approximately equal to the size of the pin and where when the plug hole is larger than the size of the pin motion of the pin is permitted in more than one axis and further including the step of selecting a plug with a plug hole with a desired size.

In another aspect, the curved radius is approximately one-half the diameter of the user appendage.

DESCRIPTION OF THE DRAWINGS

Other objects, features and advantages of the present invention will become more fully apparent from the following detailed description of the preferred embodiment, the appended claims and the accompanying drawings in which:

DETAILED DESCRIPTION OF THE INVENTION

Figure 1:
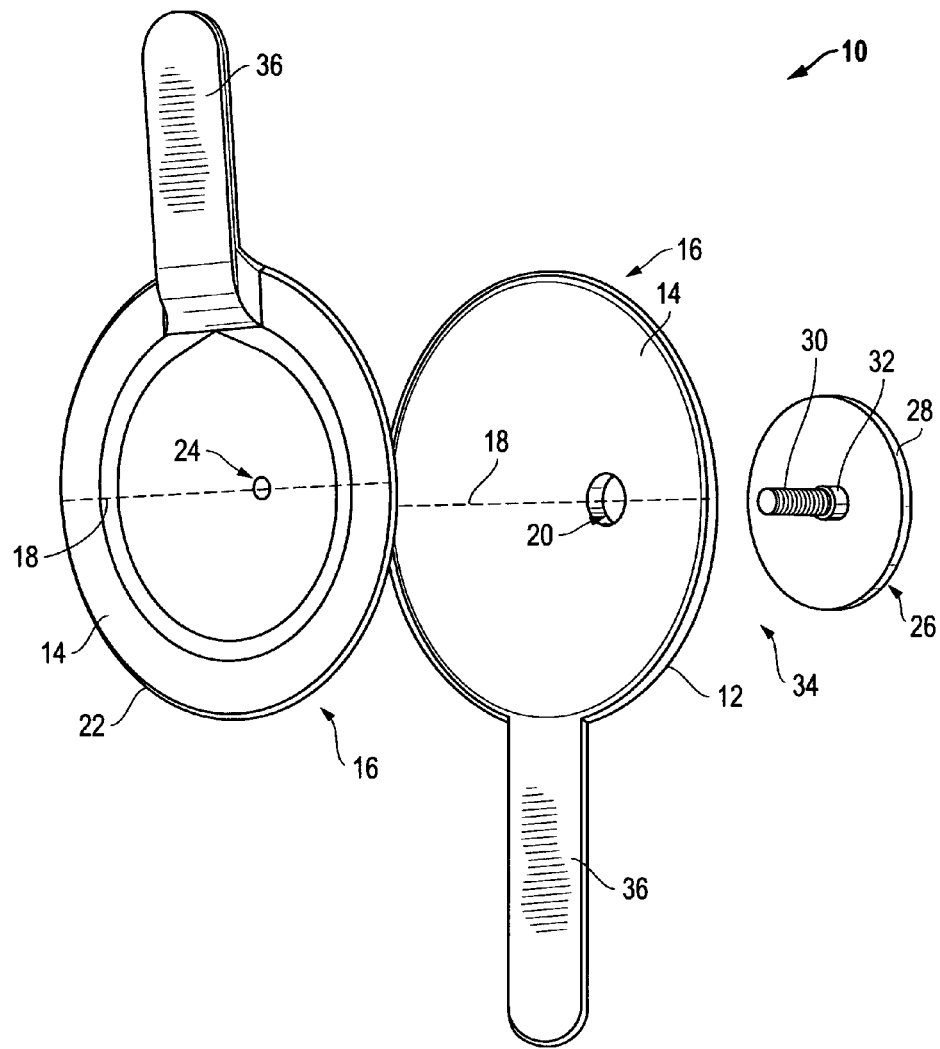
FIG. 1 is an exploded view of one embodiment of the adjustable, multi-axis, motion stabilizer apparatus showing the inside surfaces of the curved cups and a pin with a shoulder.

The preferred embodiment of the present invention is illustrated by way of example in FIGS. 1-5. With specific reference to FIGS. 1 and 2, an adjustable, multi-axis motion stabilizer apparatus 10 includes a first curved cup 12. As shown, first curved cup 12 is formed in a curved shape and includes an inside surface 14 and an outside surface 16. The inside surface 14 and the outside surface 16 are connected to form a first curved cup along a curved radius 18 (shown in a dotted line). As used herein, the term "curved radius" is given its common meaning. It should be understood that it represents a certain curvature and length. The length and curvature combine to create a particular curve. The Applicants have determined that a preferred curved radius 18 is approximately equal to one-half of the diameter of a user's appendage, such as a knee, for example only. By matching the curved radius 18 to the diameter of the user's appendage, smooth operation of the adjustable, multi-axis, motion stabilizer 10 is enabled, as will be more fully described hereafter.

Cup hole 20 extends through first curved cup 12. Second curved cup 22 includes a curved radius 18 that is approximately equal to the curved radius 18 of first curved cup 12. Second curved cup 22 also includes an inside surface 14 and an outside surface 16. The inside surface 14 and the outside surface 16 are connected to form second curved cup 22 along a curved radius 18 (shown in a dotted line). Thus, the outside surface 16 of the second curved cup 22 fits with the inside surface 14 of the first curved cup 12 as more clearly shown in FIGS. 3 and 4.

Figure 2:
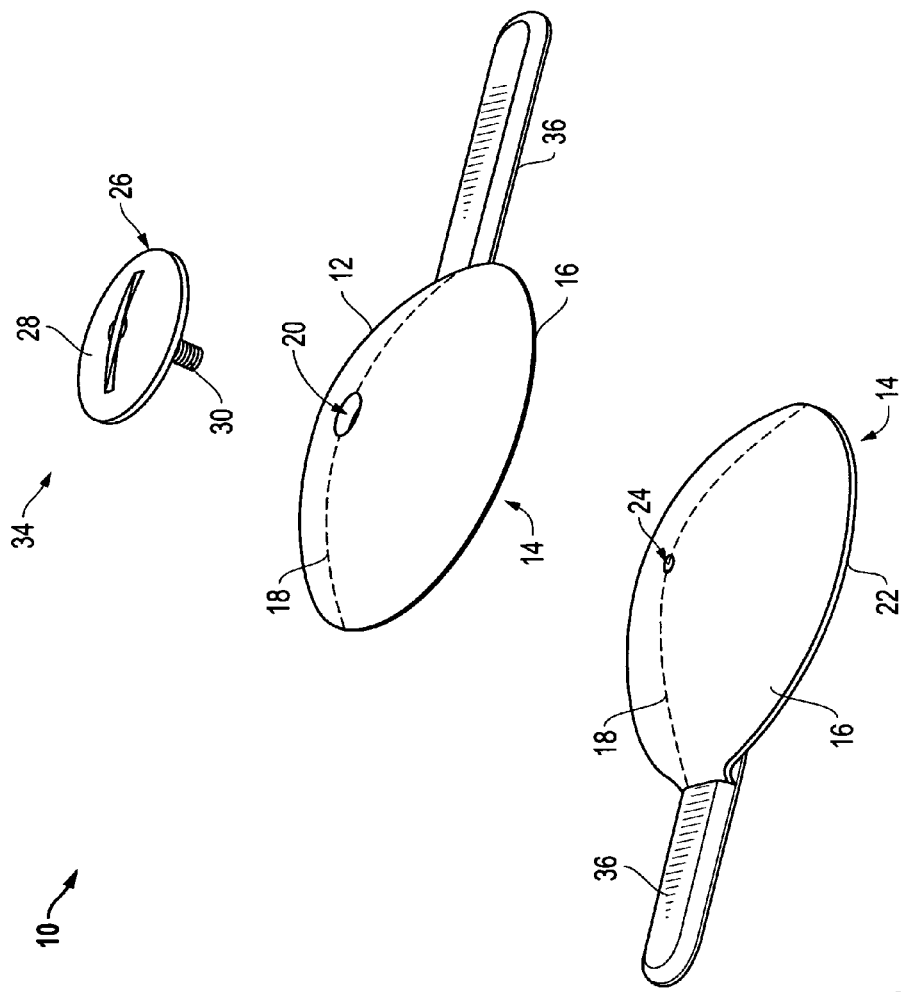
FIG. 2 is a an exploded view of the invention of FIG. 1 showing the outside surfaces of the curved cups.

Still referring to FIGS. 1 and 2, second curved cup 22 includes a hole 24. Hole 24 may or may not extend all the way through second curved cup 22. Pin 26 includes, in one embodiment, a cap 28 and a threaded shaft 30. Threaded shaft 30 may or may not include a shoulder 32. Shoulder 32 is an expanded area of threaded shaft 30. Hole 24 in second cup 22 receives the threaded shaft 30 and connects second curved cup 22 with first curved cup 12. Threaded shaft 30 does not engage cup hole 20 of first curved cup 12. In practice, threaded shaft 30 may only include threads (not shown) on the portion of the shaft that engages second curved cup 22 leaving the rest of the shaft unthreaded and smooth. In any case, first curved cup 12 freely moves around threaded shaft 30 in one direction, front to back for example.

A size adjustment device 34 for controlling movement of the pin 26 threaded shaft 30 within cup hole 20 consists of the combination of a shoulder 32 and a cup hole 20. Size adjustment device 34 enables limited motion in one direction when shoulder 32 approximately matches the size of cup hole 20. When the shoulder 32 is missing and/or when pin 26 threaded shaft 30 is smaller than hole 20, then shaft 30 is free to move in any direction up to the limit of the hole 20. In this case, motion, but controlled limited motion, is allowed in any direction or along any axis.

Still referring to FIGS. 1 and 2, extensions 36 are shown. In the embodiment where extensions 36 are present, one extension is connected with first curved cup 12 and one extension 36 may also be connected with second curved cup 22. Extensions 36 enable the combined first curved cup 12 and second curved cup 22 to be held in place where desired, such as next to a user's knee, for example only. A wrap of some sort (not shown), such as a stretchable bandage can be wrapped around the extensions 36 both above and below the knee, for example, and hold the adjustable, multi-axis motion stabilizer 10 in place as will be described more fully with regard to FIG. 5.

Figure 3:
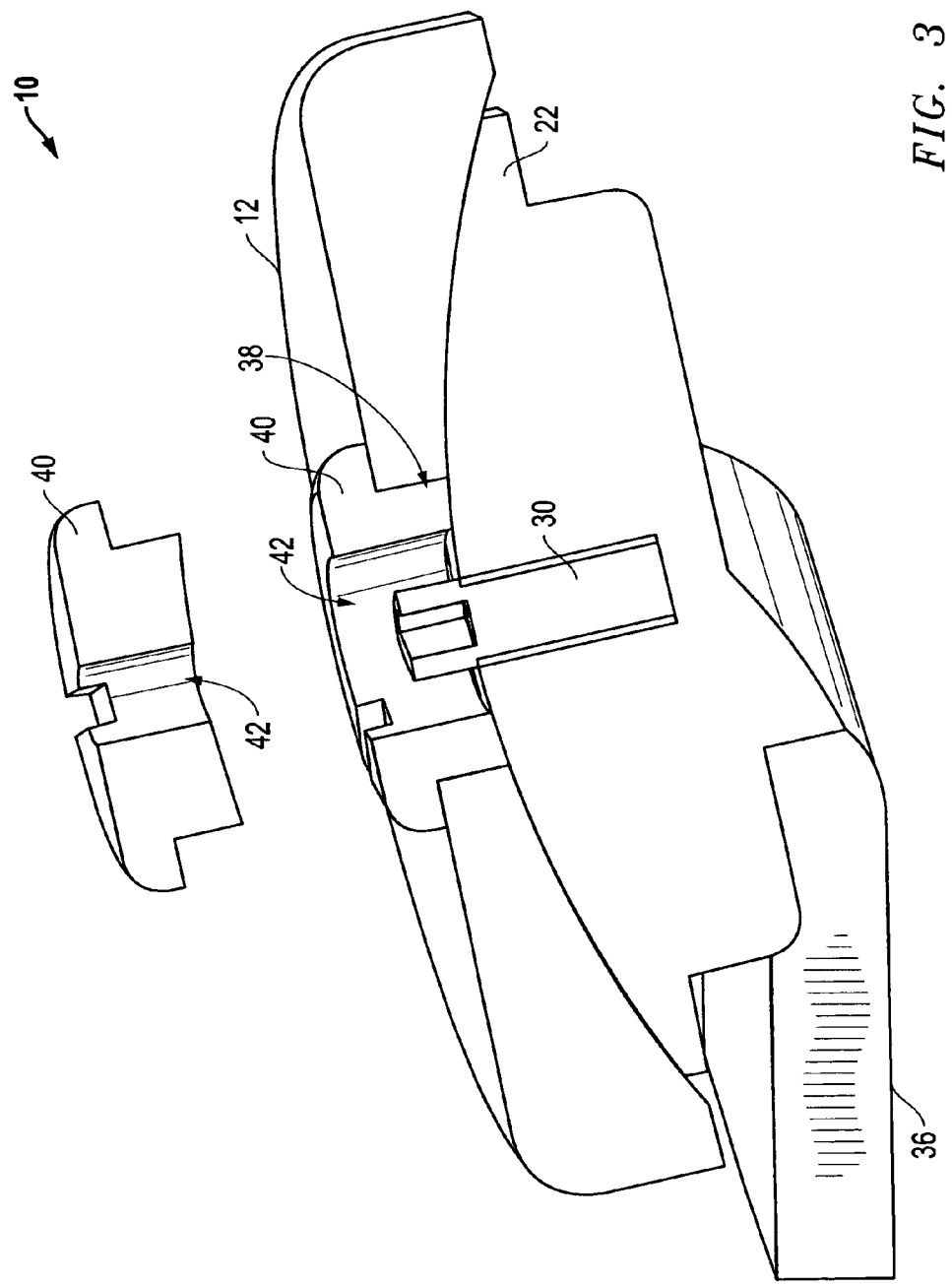
FIG. 3 is an enlarged view of another embodiment with a first cup with plugs with plug holes of two sizes and a plug recess and a second cup.
Figure 4:
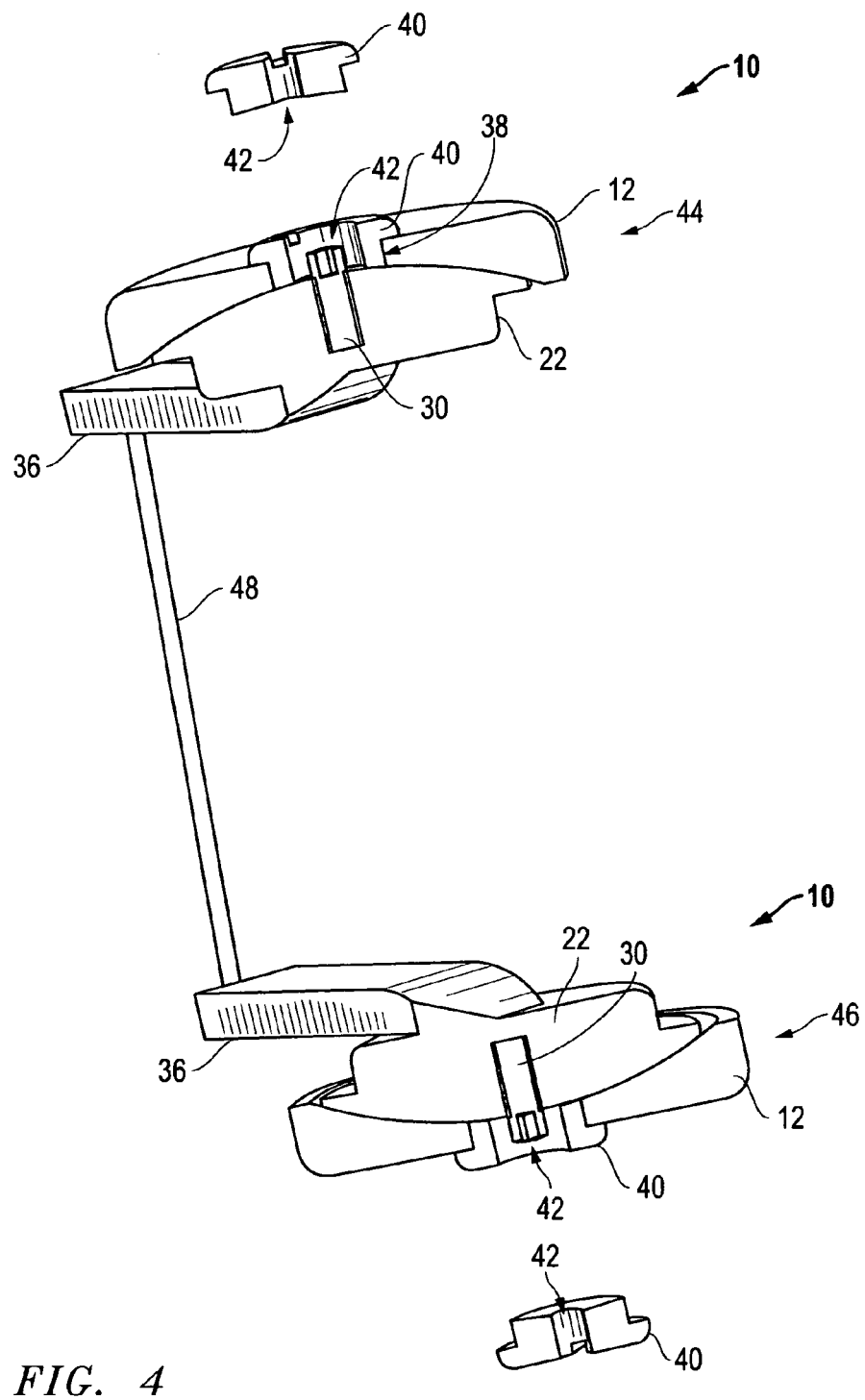
FIG. 4 is a view of the invention of FIG. 3 showing a pair of co-joined first and second cups.

Referring now to FIGS. 3 and 4, another embodiment of the adjustable, multi-axis motion stabilizer 10 is shown. In this embodiment first cup hole 12 consists of, or is replaced by, a plug recess 38 in said first cup 12. A plug 40 is provided. Plug 40 includes a plug hole 42. Plug 40 is conformed to fit in plug recess 38. In this embodiment, pin 26 includes a threaded shaft 30 screwed into second curved cup 22 as before but does not include cap 28. Instead, pin 26 threaded shaft 30 extends into plug recess 38 of first curved cup 12. Again, threaded shaft 30 may not include threads along its entire length such that the portion that extends into plug recess 38 is smooth. When multi-axis freedom of motion is desired, plug 40 with a large plug hole 42, that is a plug hole 42 bigger than the size of threaded shaft 30 is used. This is the case in FIGS. 3 and 4 with the plug 40 actually shown inserted into plug recess 38.

When only one axis of movement is desired, i.e. back and forth motion of the leg, for example only, then replacement plug 40 (shown above the inserted plug 40 in the figures) is used. This plug 40 has a plug hole 42 that is nearly equal to the size of threaded shaft 30 of pin 26. In this manner plug hole 42 limits motion of the pin 26 to motion in one axis, the back and forth direction for example.

Specifically referring to FIG. 4, the elements of the invention are shown again but in this case a first unit 44 and a second unit 46 are shown. First unit 44 and second unit 46 are formed from the combination of first cup 12 and second cup 22 as described above. Along with the other elements of the invention as described above, with either size adjustment device 34, the combination of the first curved cup 12 and the second curved cup 22 creates a unit. Once formed the units may be used individually or in combination. They may be joined by a connection bar 48 connected with two extensions 36 from the separate units when the two units 44 and 46 are intended to be used together.

Figure 5:
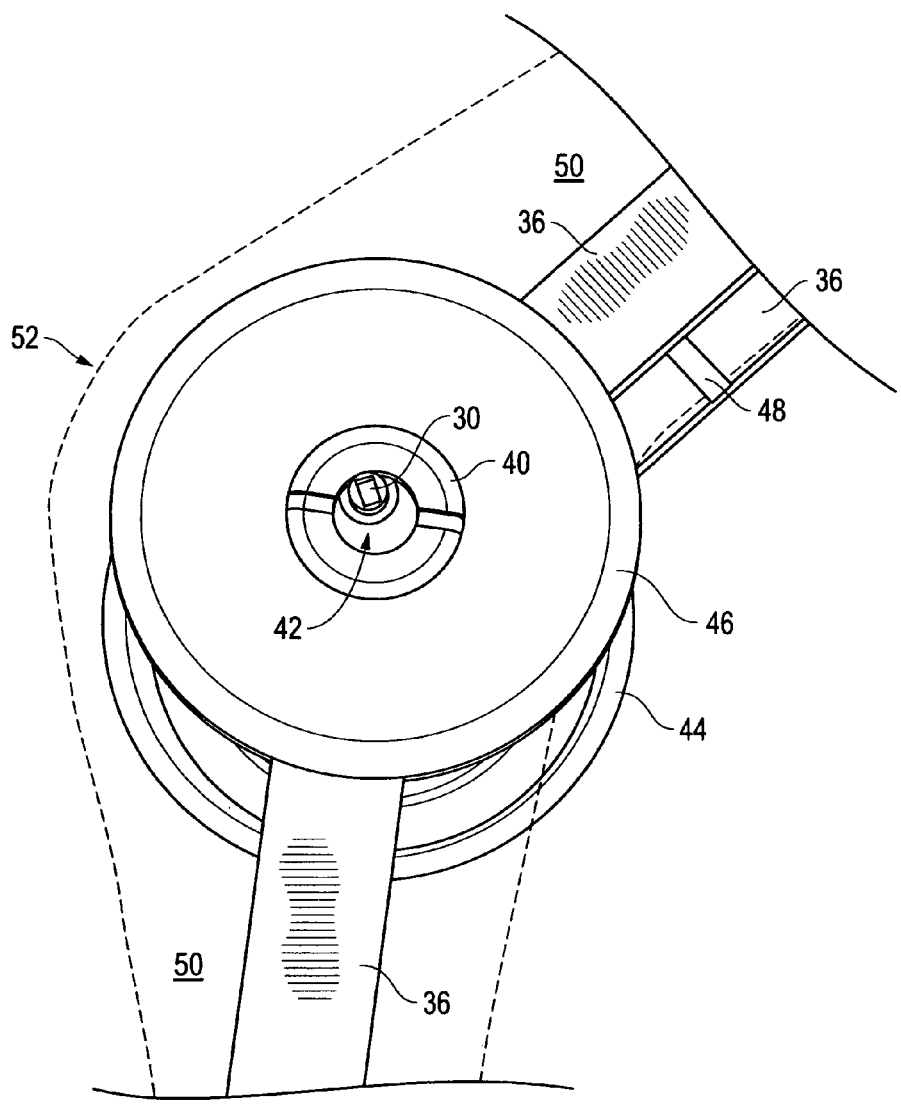
FIG. 5 is a side perspective view of the invention of FIG. 4 showing the stabilizer in place around a user's knee.

Referring now to FIG. 5, the embodiment of the invention in which a first unit 44 is connected with a second unit 46 by a connection bar 48 is shown in use with a user's appendage, in the figure a leg 50 at the knee joint 52. Extensions 36 extend above and below the knee joint 52 on leg 50 as shown. They are held in place in any convenient way and by any useful material such as, for example only, a stretchable bandage (not shown). In the Figure, the size adjustment device 34 employed is the plug 40. In this case, healing has, for example, progressed to the point that more than front to back motion is desired and required. Thus, the plug 40 includes a plug hole 42 larger than the portion of pin 26 threaded shaft 30 that extends from second curved cup 22 into plug hole 42. As a result, the outside surface 16 of second curved cup 22 is free to move over the inside surface 14 of first curved cup 12 in any direction up to the point, as shown in FIG. 5, where the shaft 30 contacts the side of the plug hole 42. By adjusting the size of the plug hole 42, again, ever increasing and/or decreasing range of motion in multiple directions is permitted in a controlled manner.

Obviously, the size adjustment device 34 consisting of the embodiment shown and described with regard to FIGS. 1 and 2 may be used in the same manner to provide adjustable, multi-axis stabilized movement. Importantly, in order that the surfaces of the cups that are in contact move smoothly, Applicants have determined that the size of the user's appendage to be protected be noted. Applicants have found that a preferred embodiment is to form the curved radius 18 of the combined first and second units 44 and 46 to approximate one-half of the diameter of the user's knee, for example only. Thus, if the user's knee is six inches in diameter, the curved radius 18 would be created to reflect a three inch curve from the center of the knee joint 52. If the user's knee is eight inches, the radius used would be four.

Applicants understand that perfect radius alignment is best but not always needed. Thus, small, medium and large units are suitable for lesser injuries and growing patients, for example. In the case of a professional athlete, for example only, exact measurements are used to create a personalized adjustable, multi-axis motion stabilizer 10.

It should also be understood that the present invention is extraordinarily well suited for use as an injury preventive device. No prior art device restricts motion of a joint beyond an acceptable point while enabling motion in all directions at the same time. Applicants' adjustable, multi-axis motion stabilizer 10 is adjustable to predetermined maximum degrees of motion in multiple directions thus providing protection against injury while enabling natural freedom of movement required for the activity.

The description of the present embodiments of the invention has been presented for purposes of illustration, but is not intended to be exhaustive or to limit the invention to the form disclosed. Many modifications and variations will be apparent to those of ordinary skill in the art. As such, while the present invention has been disclosed in connection with an embodiment thereof, it should be understood that other embodiments may fall within the spirit and scope of the invention as defined by the following claims.

What is claimed is:

1. An adjustable, multi-axis, motion stabilizer apparatus comprising:
   a. a first curved cup with a curved radius, the first curved cup with an inside surface and an outside surface;
   b. a cup hole through said first curved cup;
   c. a second curved cup with a curved radius wherein said curved radius of said second curved cup is approximately equal to the curved radius of said first curved cup, the second cup with an inside surface and an outside surface wherein said outside surface of said second curved cup fits with the inside surface of said first curved cup;
   d. a cup hole in said second curved cup;
   e. a pin conformed to fit with said cup holes and connecting said first curved cup with said second curved cup; and
   f. a size adjustment device for controlling movement of said pin within said cup holes wherein said size adjustment device is a shoulder on said pin.

2. The apparatus of claim 1 wherein said first cup hole is larger than said second cup hole and wherein said shoulder is an expanded area that approximately equals the size of said first cup hole such that said shoulder limits motion to motion in one axis.

3. The apparatus of claim 2 wherein said shoulder is smaller than said first cup hole such that motion is permitted in more than one axis.

4. The apparatus of claim 1 wherein said first cup hole comprises a plug recess in said first cup and further comprising a plug with a plug hole, the plug conformed to fit in said plug recess, wherein said plug hole limits motion of said pin to motion in one axis.

5. The apparatus of claim 4 wherein said plug hole is larger and wherein motion of said pin is permitted in more than one axis.

6. The apparatus of claim 1 further comprising a first extension connected with said first cup and a second extension connected with said second cup.

7. The apparatus of claim 6 further comprising a first unit formed from a first cup and a second cup and a second unit formed from another first cup and another second cup wherein an extension from said first unit is connected with an extension from said second unit.

8. The apparatus of claim 7 wherein said first unit and said second unit are positioned with a user appendage there between.

9. The apparatus of claim 8 wherein the curved radius is approximately one-half the diameter of the user appendage.

10. An adjustable, multi-axis, motion stabilizer apparatus comprising:
 a. a pair of first curved cups with a curved radius, the first curved cups with an inside surface and an outside surface;
 b. a first cup hole through said first curved cups wherein said first cup hole comprises a plug recess in said first cup and further comprising a plug with a plug hole, the plug conformed to fit in said plug recess;
 c. a pair of second curved cups with a curved radius wherein said curved radius of said second curved cups is approximately equal to the curved radius of said first curved cups, the second cups with an inside surface and an outside surface wherein said outside surface of said second curved cups fits with the inside surface of said first curved cups;
 d. a second cup hole in said second curved cups;
 e. a pin conformed to fit with said cup holes and connecting said first curved cups with said second curved cups wherein said plug hole limits motion of said pin to motion in one axis;
 f. extensions connected with said first curved cups and with said second curved cups; and
 g. a size adjustment device for controlling movement of said pin with said cup holes wherein said size adjustment device is said plug with said plug hole.

11. The apparatus of claim 10 wherein said first cup hole is larger than said second cup hole and said size adjustment device is a shoulder on said pin wherein said shoulder is an expanded area that approximately equals the size of said first cup hole such that said shoulder limits motion to motion in one axis.

12. The apparatus of claim 11 wherein said shoulder is smaller than said first cup hole such that motion is permitted in more than one axis.

13. The apparatus of claim 10 wherein said plug hole is larger and wherein motion of said pin is permitted in more than one axis.

14. The apparatus of claim 10 wherein an extension from one pair is connected with an extension from another pair and wherein the pairs are positioned with a user appendage there between.

15. The apparatus of claim 10 wherein the curved radius is approximately one-half the diameter of the user appendage.

16. An adjustable, multi-axis, motion stabilizer method comprising:
 a. providing a first curved cup with a curved radius, the first curved cup with an inside surface and an outside surface; a first cup hole through said first curved cup; a second curved cup with a curved radius wherein said curved radius of said second curved cup is approximately equal to the curved radius of said first curved cup, the second cup with an inside surface and an outside surface wherein said outside surface of said second curved cup fits with the inside surface of said first curved cup; a second cup hole in said second curved cup wherein said first cup hole is larger than said second cup hole; a pin conformed to fit with said cup holes and connecting said first curved cup with said second curved cup; and a size adjustment device for controlling movement of said pin with said cup holes wherein said size adjustment device is a shoulder on said pin wherein said shoulder is an expanded area of said pin and wherein when said shoulder approximately equals the size of said first cup hole said shoulder limits motion to motion in one axis and wherein when said shoulder is less than the size of the first cup hole motion is permitted in more than one axis;
 b. selecting a pin with a desired shoulder size; and
 c. connecting said first cup and said second cup to form a first unit and connecting the first unit with a user appendage.

17. The method of claim 16 wherein said first cup hole comprises a plug recess in said first cup and further comprising a plug with a plug hole, the plug conformed to fit in said plug recess, wherein said plug hole limits motion of said pin to motion in one axis when said plug hole is approximately equal to the size of said pin and wherein when said plug hole is larger than the size of said pin motion of said pin is permitted in more than one axis and further comprising the step of selecting a plug with a plug hole with a desired size.

18. The method of claim 16 wherein the curved radius is approximately one-half the diameter of the user appendage.

19. The method of claim 16 further comprising a first extension connected with said first cup and a second extension connected with said second cup.

20. The method of claim 19 further comprising a first unit formed from a first cup and a second cup and a second unit formed from another first cup and another second cup wherein an extension from said first unit is connected with an extension from said second unit and wherein said first unit and said second unit are positioned with a user appendage there between.

* * * * *